(12) United States Patent  (10) Patent No.: US 7,569,024 B1
Reznik  (45) Date of Patent: Aug. 4, 2009

(54) SHOULDER HOLDER FOR ARM SURGERY PATIENT

(76) Inventor: Alan M. Reznik, 35 Overhill Rd., Woodbridge, CT (US) 06525

( * ) Notice: Subject to any disclaimer, the term of this patent is extended or adjusted under 35 U.S.C. 154(b) by 155 days.

(21) Appl. No.: 11/505,989

(22) Filed: Aug. 18, 2006

Related U.S. Application Data

(60) Provisional application No. 60/709,129, filed on Aug. 18, 2005.

(51) Int. Cl.
*A61F 5/00* (2006.01)

(52) U.S. Cl. .......................... 602/36; 602/39

(58) Field of Classification Search ................ 248/130, 248/131, 132, 133, 135, 145, 149, 122.1, 248/124.1, 124.2, 125.2, 125.9; 602/33, 602/34, 36, 39
See application file for complete search history.

(56) References Cited

U.S. PATENT DOCUMENTS

| | | | | |
|---|---|---|---|---|
| 110,434 A | * | 12/1870 | Clarke ........................ | 248/515 |
| 1,048,750 A | * | 12/1912 | Smith .......................... | 602/34 |
| 2,718,886 A | * | 9/1955 | Sutton ......................... | 602/33 |
| 4,445,506 A | * | 5/1984 | Johansson et al. ............. | 602/39 |
| 4,616,637 A | * | 10/1986 | Caspari et al. ................ | 602/39 |
| 4,621,625 A | * | 11/1986 | Powlan ........................ | 602/33 |
| 4,671,478 A | * | 6/1987 | Schoenig et al. ......... | 248/124.1 |
| 5,279,486 A | * | 1/1994 | Harmon ................... | 248/122.1 |
| 5,401,236 A | * | 3/1995 | Summerville ................ | 602/33 |
| 5,735,806 A | * | 4/1998 | Leibovic ...................... | 602/32 |
| 6,224,026 B1 | * | 5/2001 | Dubois .................... | 248/118.3 |
| 6,390,424 B1 | * | 5/2002 | Kidushim et al. ........ | 248/122.1 |
| 6,811,541 B2 | * | 11/2004 | Lambert ...................... | 602/36 |
| 6,814,332 B2 | * | 11/2004 | Eason ..................... | 248/122.1 |
| 6,848,144 B1 | * | 2/2005 | McDonald ................. | 15/246.2 |

* cited by examiner

*Primary Examiner*—A. Joseph Wujciak, III
(74) *Attorney, Agent, or Firm*—Hoffman Wasson & Gitler

(57) ABSTRACT

A holder designed for supporting a limb, such as arm or leg, of a patient undergoing surgery has six degrees of freedom. The freedom of movement allows flexing, extending, abducting and adducting and internal and external rotation of the limb. An adjustable support extends from a vertical support. The adjustable support can slide and rotate about a horizontal and vertical axes relative to the vertical support, as well as move vertically along the vertical support. The adjustable support maintains a limb in any desired position and may be adjusted to another position quickly and easily.

10 Claims, 2 Drawing Sheets

SHOULDER HOLDER FOR ARM SURGERY PATIENT

This application claims benefit of provisional application Ser. No. 60/709,129, filed Aug. 18, 2005.

BACKGROUND OF THE INVENTION

During surgical procedures, it is necessary to maintain a limb in a particular orientation. To this end, various types of holders and supports are used to orient a limb in the proper position. It is essential that the use of the holder and the obtaining of the proper orientation be as simple and reliable as possible. This is particularly true if the surgical procedure calls for the orientation of the limb to be changed during the operation. In this instance, it is critical that the limb be moved from the first orientation to the second orientation quickly, easily and accurately.

SUMMARY OF THE INVENTION

A holder designed for supporting a limb, such as arm or leg, of a patient undergoing surgery has six degrees of freedom. The freedom of movement allows flexing, extending, abducting and adducting and internal and external rotation of the limb. An adjustable support extends from a vertical support. The adjustable support can slide and rotate about a horizontal and vertical axes relative to the vertical support, as well as move vertically along the vertical support. The adjustable support maintains a limb in any desired position and may be adjusted to another position quickly and easily.

DETAILED DESCRIPTION OF THE INVENTION

Figure 1:
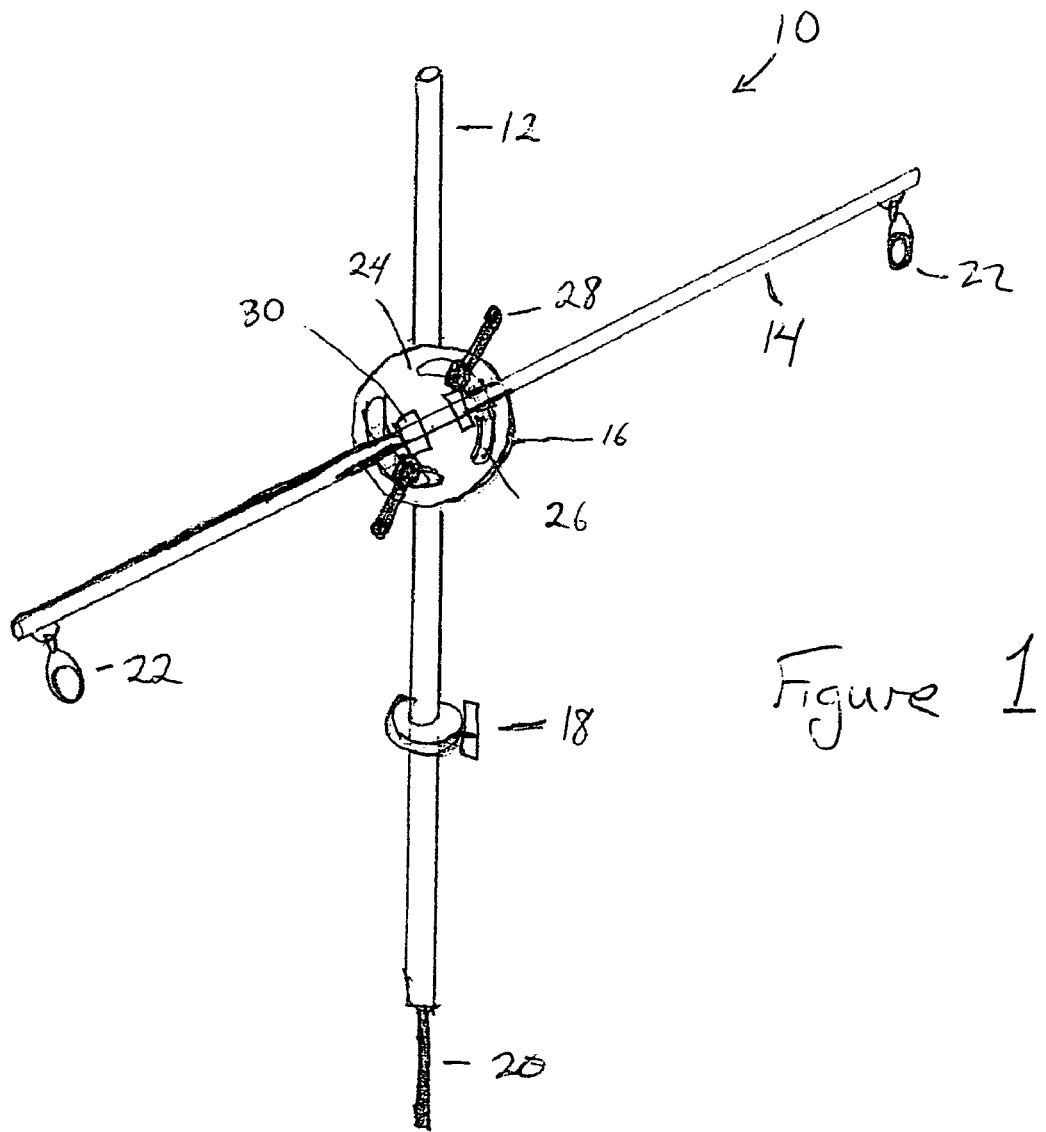
FIG. 1 is a front view of the holder.

As seen in FIG. 1, the holder 10 has a vertical support, such as a vertical pole 12 and a support pole 14 attached to the vertical pole with six degrees of freedom. A connector 16 used to attach the support pole 14 to the vertical pole allows the support pole to rotate about both a horizontal and vertical axis and well as move linearly relative to the support pole. The connector 16 can also move vertically along the support pole 12. For that reason, the vertical pole is provided with a stop 18 to limit the downward movement of the connector to prevent the connector from striking a patient.

The bottom of the vertical pole 12 has a base 20. The base may be attached to a patient support, such as an operating table, by any suitable bracket or may attach to a floor based support to provide stability for the holder.

The support pole 14 supports a cord that is attached to the patient's limb to hold the limb at any desired angular orientation. The cord may be supported by any conventional means such as extending through the support pole itself or through pulleys 22 attached to the support pole. Any number of pulleys may be used, although only two are depicted.

One type of connector that allows the desired amount of adjustments has a first circular flange 24 having a pair of arcuate slots 26 and control handles 28. The slots allow the first circular flange to be rotated and the control handles maintain the angular orientation of the first circular flange, as will be described later. A pair of collars 30 extend form the first circular flange 24. The support pole 14 extends though the collars and tightening of set screws on the collars secures the support pole in place. The position of the support pole relative to the collar can be easily adjusted.

Figure 2:
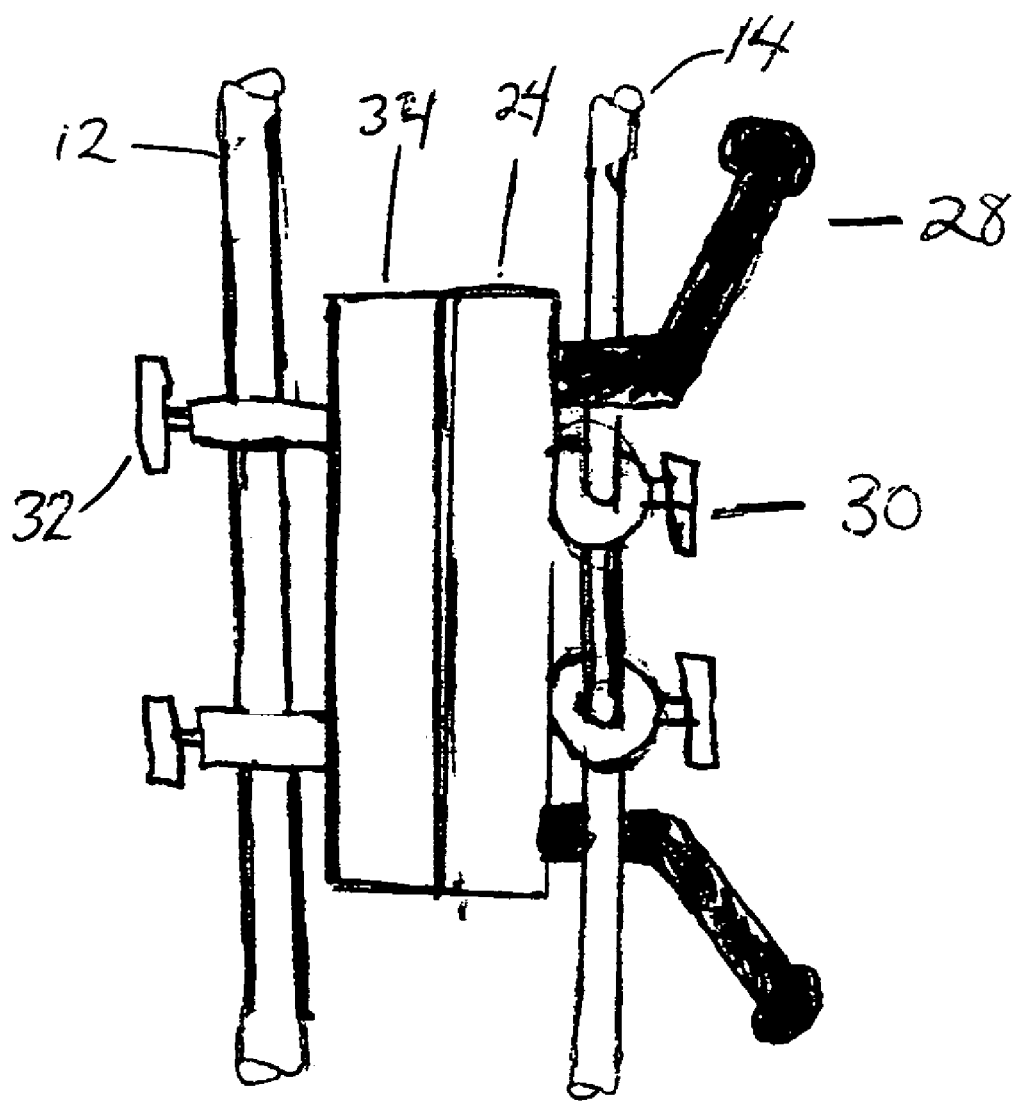
FIG. 2 is a side view of the connector.

FIG. 2 shows a close-up view of the connector 16 attached to the vertical pole 12 by collars 32, similar to collars 30, allowing the connector to be adjusted along the length of the vertical pole 12. The first circular flange 24 is rotatable connected to a second circular flange 34. Control handles extend through the first circular flange and are connected to the second circular flange by any conventional means, such as screw threads. Tightening of the control handles serves to fix the first circular flange in position.

The angular orientation of the sliding pole may also be adjusted about a vertical axis. This may be done in several ways. The vertical pole may rotate about its base. In addition, the circular flange may be rotated about the vertical pole. The loosening of the collars 32 on the flange securing it to the vertical pole, which allows vertical movement of the flange along the vertical pole, also allows the circular flanges to be rotated and secured in any desired orientation on the vertical pole.

While the invention has been described with reference to a preferred embodiment, variations and modifications would be apparent to one of ordinary skill in the art without departing from the scope of the invention. For instance, the vertical pole may have more than one support pole. Any number of connectors, such as two, can be attached to the vertical support to attach the desired number of support poles.

What is claimed is:

1. A limb positioner for supporting a limb, such as an arm or leg of a patient, having six degrees of freedom, comprising
    a vertical support,
    a connector attached to said vertical support, the connector comprising a first flange and a second flange, the second flange having a pair of arcuate slots, and a control handle extending through each slot and connected to the first flange to fix the position of the second flange relative to the first flange,
    a second support attached to said connector, said second support slidable relative to said connector,
    at least one pulley attached to said second support, and
    a cord supported by said at least one pulley.

2. The limb positioner of claim 1, wherein said pivotable connection is movable along said vertical support.

3. The limb positioner of claim 2, further comprising a stop on said vertical support to limit downward movement of said pivotable connection.

4. The limb positioner of claim 1, wherein said vertical support is a pole.

5. The limb positioner of claim 1, wherein said second support is a pole.

6. The limb positioner of claim 1, wherein said
    first flange is connected to said vertical support, and
    said second flange is rotatably connected to said first flange.

7. The limb positioner of claim 6, wherein said first flange and said second flange are circular.

8. The limb positioner of claim 1, wherein the first flange is connected to said vertical support,
    the second flange is rotatably connected to said first flange, and
    collars connected to said second flange and slidably retaining said second support.

9. The limb positioner of claim 8, wherein said first flange and said second flange are circular.

10. The limb positioner of claim 1, wherein the second support is rotatable about a vertical axis.

* * * * *